(12) United States Patent
Abelino De Leon Martin et al.

(10) Patent No.: US 8,884,026 B2
(45) Date of Patent: Nov. 11, 2014

(54) PROCESS FOR PREPARING RUFINAMIDE INTERMEDIATE

(75) Inventors: Antonio Abelino De Leon Martin, Barbera Del Valles (ES); Jordi Bessa Bellmunt, Barcelona (ES); Juan Huguet Clotet, Sant Joan Despi (ES); Lluis Sola Carandell, Tarragona (ES); Gloria Freixas Pascual, Tarragona (ES); Jordi Ceron Bertran, Tarragona (ES); Pere Dalmases Barjoan, Sant Feliu De Llobregat (ES)

(73) Assignee: Laboratorios Lesvi, S.L. (ES)

( * ) Notice: Subject to any disclaimer, the term of this patent is extended or adjusted under 35 U.S.C. 154(b) by 0 days.

(21) Appl. No.: 13/643,717

(22) PCT Filed: May 2, 2011

(86) PCT No.: PCT/EP2011/056986
§ 371 (c)(1),
(2), (4) Date: Oct. 26, 2012

(87) PCT Pub. No.: WO2011/135105
PCT Pub. Date: Nov. 3, 2011

(65) Prior Publication Data
US 2013/0045998 A1 Feb. 21, 2013

Related U.S. Application Data

(60) Provisional application No. 61/331,107, filed on May 4, 2010.

(30) Foreign Application Priority Data

Apr. 30, 2010 (EP) .................................... 10161546
Dec. 14, 2010 (EP) .................................... 10194881

(51) Int. Cl.
*C07D 249/04* (2006.01)
*A61K 31/4192* (2006.01)

(52) U.S. Cl.
CPC .......... *C07D 249/04* (2013.01); *A61K 31/4192* (2013.01)
USPC .......................................... 548/255

(58) Field of Classification Search
USPC .......................................... 548/255
See application file for complete search history.

(56) References Cited

U.S. PATENT DOCUMENTS
4,789,680 A 12/1988 Meier

FOREIGN PATENT DOCUMENTS

| EP | 0994863 | 12/1998 |
|---|---|---|
| EP | 0994864 | 12/1998 |
| WO | WO98/56772 | 12/1998 |
| WO | WO98/56773 | 12/1998 |
| WO | WO2010/043849 | 4/2010 |

OTHER PUBLICATIONS

PCT Search Report and Written Opinion for PCT/EP2011/056986, completed May 10, 2011.

*Primary Examiner* — Samantha Shterengarts
(74) *Attorney, Agent, or Firm* — Barnes & Thornburg LLP

(57) ABSTRACT

The present invention refers to an improved method for the preparation of compound 1-(2,6-difluorobenzyl)-1H-1,2,3-triazole-4-carboxylic acid substantially free of its 3H-I isomer. The invention also refers to the use of said intermediate for the preparation of Rufinamide and for obtaining a new polymorphic form of Rufinamide, designed as Form R-5. The invention also refers to said new polymorph of Rufinamide, and to the composition containing it and its use as medicament. The new polymorph of Rufinamide shows good stability and appropriate physico-chemical properties for its manipulation on industrial scale. Polymorph Form R-5 will be suitable to use as pharmaceutical for the treatment of convulsions, especially for the treatment of epilepsy.

14 Claims, 3 Drawing Sheets

PROCESS FOR PREPARING RUFINAMIDE INTERMEDIATE

CROSS-REFERENCE TO RELATED APPLICATIONS

This application is a national stage entry under 35 U.S.C. §371(b) of International Application No. PCT/EP2011/056986, filed May 2, 2011, which claims the benefit of European Patent Application Serial No. 10161546.6, filed Apr. 30, 2010 and European Patent Application Serial No. 10194881.8, file Dec. 14, 2010, the disclosures of all of which are hereby incorporated herein by reference.

FIELD OF THE INVENTION

The present invention refers to a method for the preparation of compound 1-(2,6-difluorobenzyl)-1H-1,2,3-triazole-4-carboxylic acid (1H-I) substantially free of its 3H-isomer. The invention also refers to the use of said intermediate for the preparation of Rufinamide and for obtaining a new polymorphic form of Rufinamide. The invention also refers to a new polymorphic form, referred herein as R-5.

BACKGROUND OF THE INVENTION

Rufinamide presents an anticonvulsant activity and it is used in epileptics with partial and generalized tonic-clonic convulsions. Its chemical name is 1-(2,6-difluorobenzyl)-1H-1,2,3-triazole-carboxamide having the following structure:

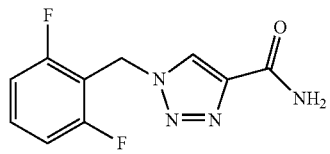

Rufinamide

Rufinamide was first disclosed by the American patent U.S. Pat. No. 4,789,680 to Ciba-Geigy. Scheme 1 shows the preparation of Rufinamide as described therein. As it is taught, Rufinamide is prepared from intermediate 1-(2,6-difluorobenzyl)-1H-1,2,3-triazole-4-carboxylic acid (1H-I) by treatment with thionyl chloride followed by addition of concentrated aqueous ammonia solution. Finally, Rufinamide is recrystallised from ethanol (Scheme 1)

Scheme 1

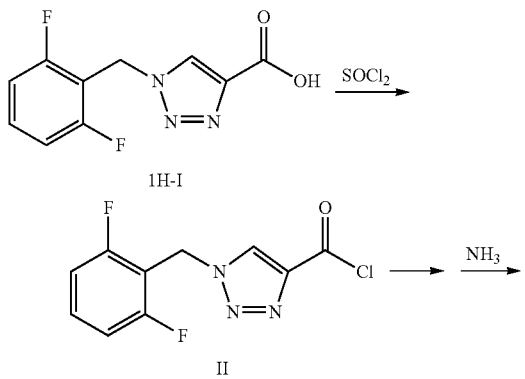

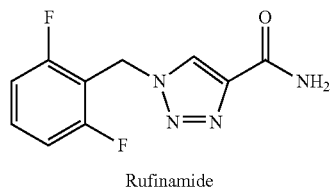

Rufinamide

Compound 1H-I is prepared from 2,6-difluorobenzyl azide (IV) and propiolic acid.

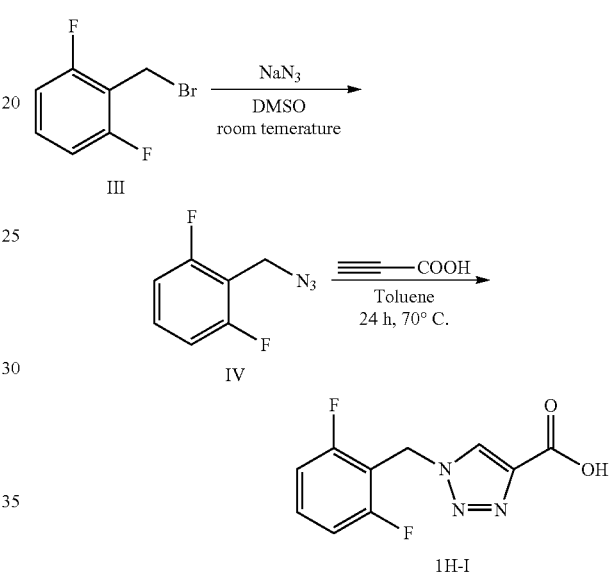

The process of Scheme 2, that is, the preparation of intermediate 1-(2,6-difluorobenzyl)-1H-1,2,3-triazole-4-carboxylic acid (1H-I), has been found to have several disadvantages like lengthy reaction times and the usage of high boiling point solvents like dimethyl sulfoxide (DMSO).

Zheshan et al. in Progress in Natural Science, 16, 9, 925-929 describe the preparation of 1-substituted benzyl-N-substituted-1,2,3-triazole-4-formamides through reaction of substituted benzyl chloride and sodium azide, subsequent cyclization with ethyl propiolate and, finally, the amidation of the resulting ester derivative (Scheme 2).

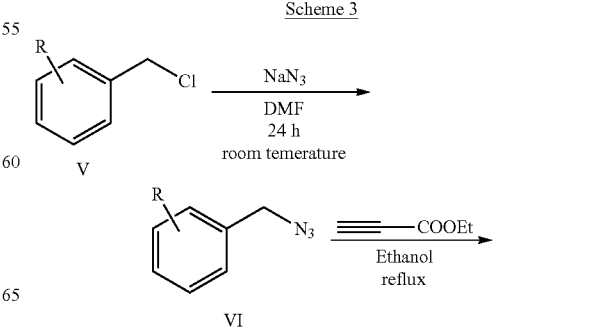

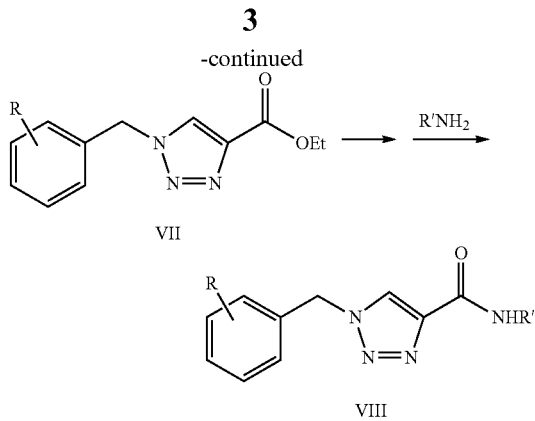

VII

VIII

The process of Scheme 3 requires high temperatures, long reaction times and the use of a high boiling solvent like DMF. All these aspects are process concerns that must be addressed when considering the process for production in pilot-plant or with manufacturing-scale equipment.

All above processes purify the alkyl azide via distillation or under pressure which are extremely hazardous and can result in explosion.

International patent application WO 2010/043849 describes a process for the preparation of Rufinamide characterized in that no isolation of chemical intermediates is required. The process comprises the reaction between 2,6-difluorobenzylbromide and sodium azide. The solvent reaction is water and the reaction is completed after approximately, 30 hours at 70-75° C. Then, methyl propiolate is added. After the reaction was completed, aqueous ammonia is added to obtain Rufinamide. The formation of 2,6-difluorobenzylazide in the presence of water and at 70-75° C. yields the product after 30 hours of reaction. These conditions are not suitable for large scale production due to the formation of hydrazoic acid which is extremely explosive.

In all these processes, the formation of the triazole ring inevitably produces mixtures of isomers 1H and 3H. However, only the 1H-isomer produces Rufinamide.

There is a need for processes for the preparation of compound 1H-I substantially free of its 3H-isomer that are environmentally friendly, easy to practice, produce high yields of the required product, less costly and that can be adapted to industrial scale. The resulting carboxylic acid derivative will be used to prepare Rufinamide.

On the other hand, European patents EP0994 863 and EP0994864 disclose polymorphic forms of Rufinamide referred as, crystal modification A, A', B and C. According to the teachings of these patents, crystal modifications A or A' have better thermodynamic stability than crystal modifications B and C. Crystal modification C, the least stable of the three crystal modifications, can only be obtained under very specific conditions.

However, it has been experimentally found that the crystal modification C is rapidly converted into modification B at room temperature within a few weeks. The modification C is also converted into either the modification A or A' or into the modification B, depending on experimental conditions. Moreover, the modification A or A' has a slower dissolution rate in water or in gastric fluid (so-called "slow-release effect").

One of the most desirable properties of a pharmaceutical compound, which can form different polymorphs (that is the case of Rufinamide), is its solubility in aqueous solution, in particular the solubility of said compound in the gastric juices of a patient. Another important property relates to the ease of processing the polymorphic form into pharmaceutical dosages, as the tendency of a powdered or granulated form to flow as well as the surface properties, determine whether the crystals of said polymorphic form will adhere to each other when compacted into a tablet.

The discovery of new polymorphic forms and solvates of a pharmaceutically useful compound provides a new opportunity to improve the performance characteristics of a pharmaceutical product such as improved stability, solubility and/or impurity profile. It enlarges the repertoire of materials that a formulation scientist has available for designing, for example, a pharmaceutical dosage form of a drug with a targeted release profile or other desired characteristic.

BRIEF DESCRIPTION OF THE INVENTION

The present invention is related to an improved method for the preparation of 1-(2,6-difluorobenzyl)-1H-1,2,3-triazole-4-carboxylic acid (I) substantially free of its 3H-isomer and its use so-prepared for the obtaining of Rufinamide.

Thus, a first aspect of the invention relies on a one-pot process for the preparation of compound of formula 1H-I substantially free of 3H-I isomer

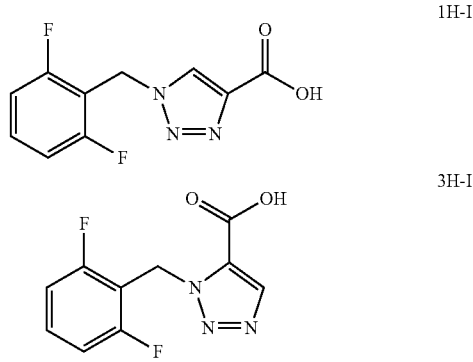

which comprises
a) reacting a compound of formula IX:

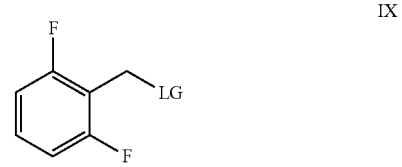

IX wherein LG is a leaving group
with sodium azide in the presence of a phase transfer catalyst and a non polar solvent or a dipolar aprotic solvent having a boiling point below 100° C.,
b) reacting the resulting mixture with propiolic acid; and
c) isolating compound 1H-I A second aspect of the invention relates to a process for the preparation of Rufinamide which comprises the use of compound 1H-I prepared as indicated in the first aspect.

A third aspect of the invention is a process for making a pharmaceutical composition comprising Rufinamide, which process comprises Rufinamide prepared from intermediate compound of formula 1H-I obtained according to the process of the invention.

A fourth object of the present invention is to provide a process for obtaining a new polymorphic form of Rufinamide with good yields, named R-5, which comprises the use of compound 1H-I prepared as indicated in the first aspect.

Still another object of the invention is the new polymorphic form of Rufinamide named R-5 which is characterized by X-ray powder diffraction pattern, DSC thermogram, IR spectrum and TGA thermogra. The Inventors of the present invention have surprisingly found that Rufinamide can further exist in a new polymorphic form, referred herein as R-5, which shows good stability and appropriate physico-chemical properties for its manipulation at industrial scale. As a result of that, the polymorphic form R-5 of the invention will be suitable to be used in pharmaceutical compositions showing advantages over known crystalline forms of Rufinamide due to the improvement in the performance characteristics such as stability (milling, grinding), solubility and/or impurity profile.

Finally, the invention is also directed to the use of said polymorphic form R-5 of Rufinamide for the treatment of convulsions of various origins such as for the treatment of epilepsy.

DETAILED DESCRIPTION OF THE INVENTION

Figure 1:
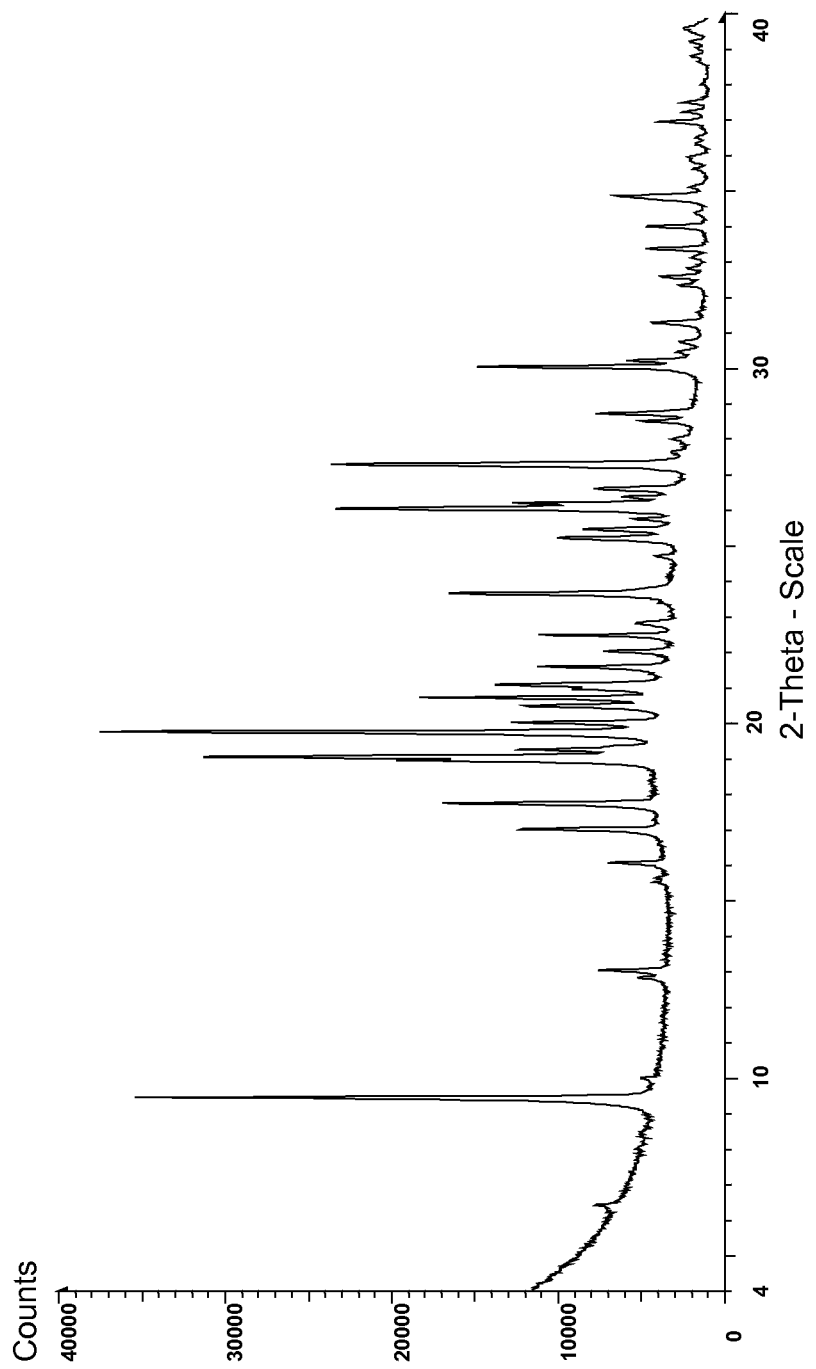
FIG. 1 shows the X-ray powder diffraction pattern (XRPD) of polymorphic form R-5 of Rufinamide.

When two chemical stages are involved in the production of a new compound it is always desirable, from the economic point of view, to perform both stages in the same pot without isolating the intermediate. However, it is difficult, in most cases, to obtain a product of high purity if the intermediate is not isolated and purified, since by-products of the first stage also become involved in the chemistry of the second stage, increasing the range of impurities formed in the process. The process of the invention makes it possible to obtain a product of high isomeric purity even when the intermediate was not isolated and the process was performed in a one-pot manner.

The term "one-pot process", used herein, means two or more reactions that take place without isolating intermediate compounds, wherein all the reactants are added at the beginning of the first reaction or adding all reactants sequentially during the course of the reaction.

As used herein, "substantially free of the 3H-isomer" refers to compound 1H-I comprising 3H-isomer in an amount of less than about 0.2 area-% as measured by a chromatographic method such a HPLC or UPLC. Specifically, the 1H-isomer, as disclosed herein, contains less than about 0.15 area-%, more specifically less than about 0.10 area-%, still more specifically less than about 0.05 area-% of its 3H-isomer.

As used herein, "low boiling dipolar aprotic solvent" refers to a dipolar aprotic solvent with a boiling point below 100° C.

The term "leaving group" refers to a group that can easily be replaced by another group. In J. March Advanced Organic Chemistry, 4th edition, 1992, are listed some typical leaving groups. In the context of the present invention, the leaving groups are preferably selected from halogens and activated alcohols, such as sulphonyloxy groups. The halogens include fluorine, chlorine, bromine and iodine. Preferably, the leaving group is chlorine and bromine The sulphonyloxy group is represented by —OSO$_2$R, wherein R is a substituted or unsubstituted alkyl, a substituted or unsubstituted aryl, a fluorinated hydrocarbon or a halogen. Preferably R is methyl, p-tolyl, trifluoromethyl or fluorine.

The authors have reproduced prior art processes for the preparation of compound of formulae 1H-I (as per Scheme I) and compound VII (R=2,6-F$_2$, Scheme II). Generally speaking, these compounds are prepared through two different steps 1) and 2), which comprise:

1) preparing 2,6-difluorobenzyl azide from 2,6-difluorobenzyl halide and sodium azide and 2) reacting the isolated product of step 1) with propiolic acid or ethyl propiolate The reproduction of the process described in U.S. Pat. No. 4,789,680 yields compound I wherein 2.85 area-% corresponds to isomer 3H.

The reproduction of the process described in Zheshan et al. for the preparation of compound VII (R=2,6-F$_2$) results in the obtaining of a mixture of isomers which contains from 20 to 30% (w/w) of the 3H-isomer. Then, the recrystallization from methanol yields exclusively the 1H-isomer.

Unexpectedly, the inventors have found that when performing both steps, 1) and 2), as a one-pot process, the resulting product, the 1H-isomer, before being isolated, is obtained substantially free of its 3H-isomer.

According to the first aspect of the invention, it is provided a one-pot process for the preparation of compound of formula 1H-I substantially free of 3H-I isomer, a compound of formula 1H-I comprising 3H-isomer in an amount of less than about 0.2 area-%,

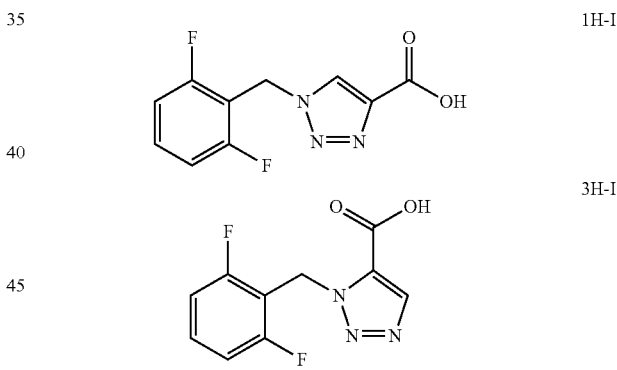

which comprises
a) reacting a compound of formula IX:

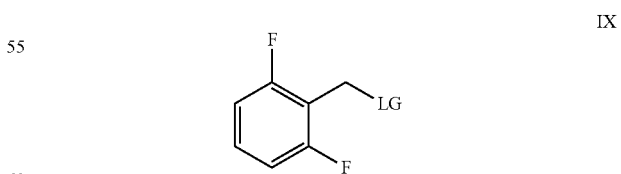

wherein LG is a leaving group
with sodium azide in the presence of a phase transfer catalyst and a non polar solvent or a low boiling dipolar aprotic solvent,
b) reacting the resulting mixture with propiolic acid; and
c) isolating compound 1H-I.

The authors have surprisingly found that the use of non polar solvents or a low boiling solvent or mixtures thereof in step a) substantially reduces the formation of hydrazoic acid. As known, hydrazoic acid is a colorless, volatile, highly toxic and extremely explosive liquid at room temperature and pressure.

In addition, the use of a phase transfer catalyst facilitates the reaction of sodium azide in non polar or low boiling dipolar aprotic solvents allowing completing the azidation in reasonable time and at a low reaction temperature.

The non polar solvent is insoluble or slightly soluble in water. Preferred non polar solvents are heptane, methyl cyclohexane, hexane, pentane, toluene and mixtures thereof. Low boiling dipolar aprotic solvents used in the invention comprise dipolar aprotic solvents with boiling points below 100° C. Low boiling dipolar solvents that can be used in the invention are selected from, ethyl acetate, isopropyl acetate, acetone, tetrahydrofuran and mixtures thereof. Most preferred solvents are toluene as a non polar solvent and isopropyl acetate as a low boiling dipolar solvent with a boiling point below 100° C.

The reaction between 2,6-difluorobenzyl chloride and sodium azide can be performed at a temperature between 0-100° C., preferably between 15-50° C. and more preferably between 20-25° C. Once the reaction is completed, the obtained mixture is washed and propiolic acid is added.

According to a preferred embodiment, the phase transfer catalyst is selected from tetralkylammonium salts, 18-crown-6, phosphonium salts, cryptands and doped clays. Preferably, the phase transfer catalyst is tetra-n-butylammonium bromide. An amount of 1 to 10%, preferably, 5% molar of catalyst is used.

Most preferred compounds of formula IX are those wherein LG is selected from halogens and activated alcohols, such as sulphonyloxy groups. The halogens include fluorine, chlorine, bromine and iodine. Preferably, LG is selected from chlorine and bromine.

Propiolic acid may be added directly or in the form of a solution with water or with an organic solvent or mixtures thereof. The election of the most suitable organic solvent is a matter of routine experimentation for the skilled person. Examples of solvents that can be used are polar solvents such methanol, ethanol, isopropanol, butanol, etc. Preferably, propiolic acid is added in form of a solution with water.

The reaction with propiolic acid can be performed between 20-65° C., preferably, 50-55° C. This temperature is maintained during 8-10 hours, preferably 8 hours.

The inventors have found that the yield of the reaction increases as the amount of propiolic acid is increased. Preferably, 1.2 to 2 equivalents of propiolic acid may be used. More preferably, 1.5 equivalents of propiolic acid are used.

The resulting 1H-I isomer is isolated from the reaction mixture by precipitation at a pH value between 3.0 and 4.5, preferably between 3.2 and 4.0.

The process may comprise a further step d) of purification of 1-(2,6-difluorobenzyl)-1H-1,2,3-triazole-4-carboxylic acid to achieve a purer compound. For example, the 1H-isomer can be further purified by repeating cycles of dissolution in water at pH 12 and precipitation at pH 3.2-4.0. The inventors have confirmed that this process is a general methodology for the purification of compound 1H-I from a mixture of both compounds 1H-I and 3H-I. Thus, the invention also covers a process for the purification of compound 1H-I from a mixture of compounds 1H-I and 3H-I which comprises the dissolution of the mixture at a pH≥12 and precipitation at pH 3.2-4.0.

The inventors have also used the one-pot process of the invention in the preparation of compound 1-(2,6-Difluorobenzyl)-1H-[1,2,3]triazole-4-carboxylic acid ethyl ester. The one-pot process of the invention (in this case, ethyl propiolate is used instead of propiolic acid) yields the desired 1H-isomer of the propiolic ester in good yields. This one-pot process comprises the reaction of 2,6-difluorobenzyl chloride with sodium azide in the presence of a phase transfer catalyst (i.e. TBAB) and a low boiling dipolar aprotic solvent (i.e. isopropyl acetate). Then, from 1.3 to 2 eq of ethyl propiolate are added in the presence of a polar solvent, preferable ethanol. The resulting isomeric mixture of 1H- and 3H-ester derivatives are isolated by recrystallisation from methanol.

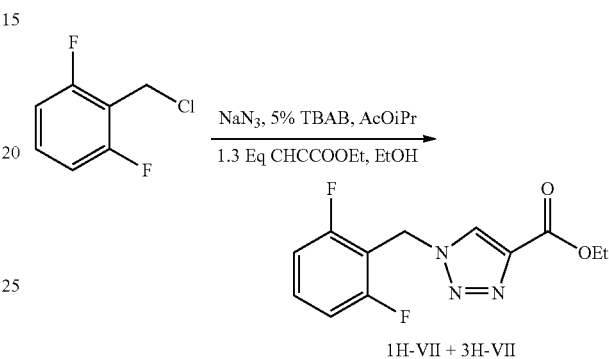

1H-VII + 3H-VII

A second aspect of the invention provides a process for the preparation of Rufinamide which comprises the use of 1-(2,6-difluorobenzyl)-1H-1,2,3-triazole-4-carboxylic acid prepared according to the process of the invention. This process comprises the activation of compound 1H-I followed by reaction of ammonia or a solution containing ammonia. The activation of compound 1H-I is in the form of an acid halide, preferably, chloride. There are several reagents to activate compound 1H-I in the form of an acid chloride such as oxalyl chloride and thionyl chloride.

The invention also includes a process for making a pharmaceutical composition comprising Rufinamide, which process comprises Rufinamide prepared from intermediate compound 1H-I, obtained according to the process of the invention, and using Rufinamide so made to make the said pharmaceutical composition.

The invention may also comprise further purification of crude Rufinamide to achieve a highly pure compound. Preferably, Rufinamide is purified by recrystallisation from ethanol.

Rufinamide obtained according to the process of the present invention can be milled or micronised to obtain a $D_{50}$ and $D_{90}$ particle size of less than about 400 μm, preferably less than about 200 μm, more preferably less than about 150 μm, still more preferably less than about 50 μm and most preferably less than 15 μm. It is noted the notation $D_x$ means that X % of the particles in a composition have a diameter less than a specified diameter D. Thus, a $D_{50}$ of about 400 μm means that 50% of the micronised rufinamide particles have a diameter less than 400 μm.

Particles of this size are obtained by conventional methods, conventional dry size reduction in the pharmaceutical industry is accomplished by impact. This impact size reduction generally falls into two categories: mechanical impact and impact via fluid energy. Examples of mechanical impact mills are hammer and screen mills and pin mills, while spiral jet mills, loop jet mills, and fluidized bed jet mills are examples of micronizers or fluid energy mills.

Several polymorphic forms of Rufinamide (A, B and C) have been described (see patents EP 0 994 863 B1 and EP 0 994 864 B1).

The inventors have discovered a new polymorphic form R-5 which can be obtained by the following steps:
  (a) providing a solution of 1-(2,6-difluorobenzyl)-1H-1,2,3-triazole-4-carbonyl chloride in anhydrous tetrahydrofuran;
  (b) generating ammonia in-situ while maintaining the pH of the mixture below 9 to obtain a precipitate; and
  (c) recovering the crystalline form R-5 of Rufinamide 1-(2,6-difluorobenzyl)-1H-1,2,3-triazole-4-carbonyl chloride used in step (a) may be prepared from 1-(2,6-difluorobenzyl)-1H-1,2,3-triazole-4-carboxylic acid substantially free of 3H-I isomer as described above.

In the present invention, the expression "generating ammonia in-situ" means that no addition of ammonia is carried out and that the ammonia which allows the reaction with 1-(2,6-difluorobenzyl)-1H-1,2,3-triazole-4-carbonyl chloride is generated or built in the same reaction media. The formation of ammonia is achieved by combining an ammonium salt with a base with a pKb lower than of ammonia. Surprisingly, the authors of the present invention have found that the reaction of 1-(2,6-difluorobenzyl)-1H-1,2,3-triazole-4-carbonyl chloride with the ammonia generated in-situ in the reaction media allows to obtain a new polymorphic form R-5, which has advantage compared to the known polymorphic forms of Rufinamide. See the experimental data included above. For example, ammonia may be formed in-situ when using ammonium chloride and sodium bicarbonate.

Step (b) may be performed in the absence or in the presence of water. Another object of the present invention is a pharmaceutical composition comprising a therapeutically effective amount of polymorphic form R-5 of Rufinamide defined above, together with an appropriate amount of pharmaceutically acceptable excipients and carriers.

The above compositions can be administered by any suitable route. As stated above, the polymorphic form R-5 of Rufinamide for the manufacture of a medicament for the treatment of convulsions of various origins, for example for the treatment of epilepsy is also encompassed by the present invention.

Figure 2:
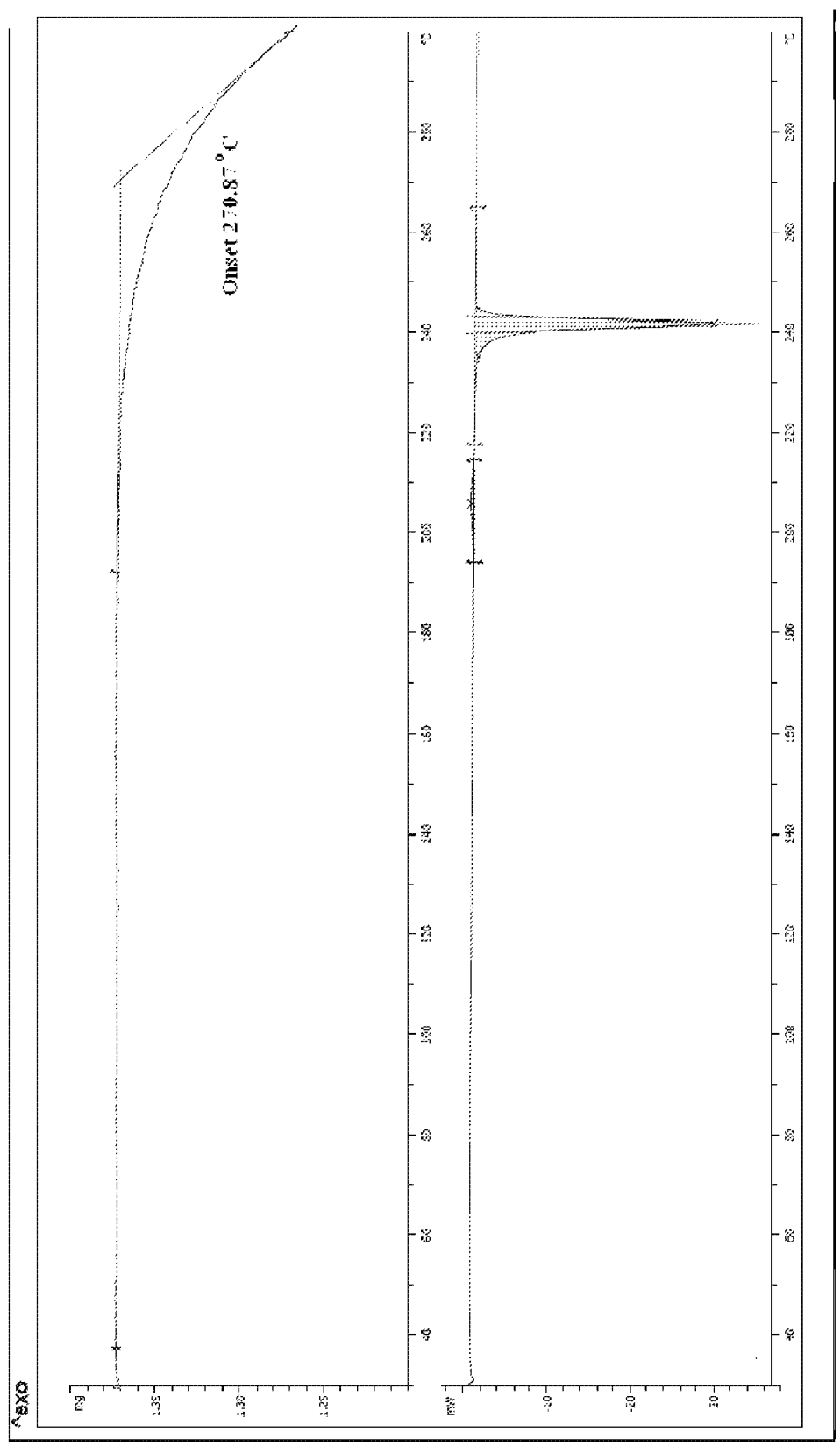
FIG. 2 shows the differential scanning calorimetry (DSC) and the thermogravimetric analysis (TGA) of polymorphic form R-5 of Rufinamide.
Figure 3:
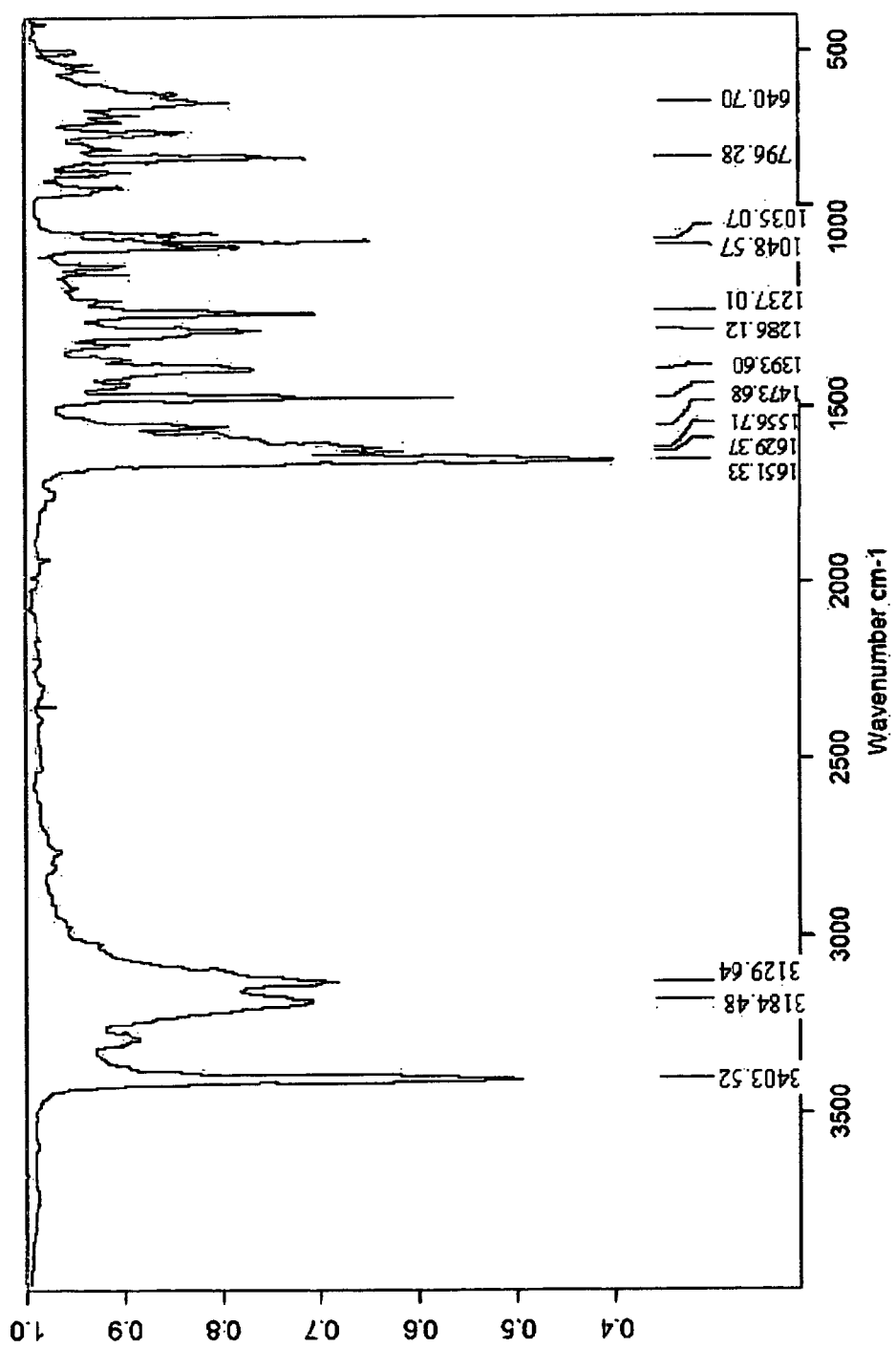
FIG. 3 shows the infrared (IR) spectrum of polymorphic form R-5 of Rufinamide.

According to the invention, a new polymorphic form of Rufinamide, referred as form R-5, which is characterized by its X-ray powder diffraction pattern (FIG. 1), its DSC thermogram and thermogravimetric analyses (FIG. 2) and its infrared (IR) spectra (FIG. 3) is also provided.

XRD patterns was obtained using an analytical X'Pert PRO MPD alpha 1 powder diffractometer, equipped with a CuKα source (λ=1.54056 Å) and a X'Celerator Detector, which operates at 40 kV and 40 mA. Each sample was scanned between 4 and 40° in 2θ, with a step size of 0.016° and a scan rate of 40 s/step. The PXRD of crystalline phase R-5 of Rufinamide are depicted in Table 1 and FIG. 1.

TABLE 1

| Angle 2θ[1] (°) | Relative Intensity % |
| --- | --- |
| 6.4 | 20.1 |
| 9.4 | 85.1 |
| 9.9 | 12.8 |
| 12.8 | 13.2 |
| 13.0 | 19.6 |
| 15.5 | 10.8 |
| 15.7 | 10.4 |

TABLE 1-continued

| Angle 2θ[1] (°) | Relative Intensity % |
| --- | --- |
| 16.0 | 17.9 |
| 17.0 | 32.1 |
| 17.7 | 44.6 |
| 18.9 | 52.4 |
| 19.0 | 83.4 |
| 19.2 | 32.5 |
| 19.7 | 100.0 |
| 20.0 | 33.6 |
| 20.5 | 31.7 |
| 20.7 | 48.4 |
| 21.0 | 24.1 |
| 21.1 | 36.3 |
| 21.6 | 29.5 |
| 22.0 | 18.7 |
| 22.5 | 29.2 |
| 22.8 | 13.5 |
| 23.7 | 43.8 |
| 24.7 | 10.4 |
| 25.2 | 26.4 |
| 25.5 | 22.0 |
| 25.8 | 14.1 |
| 26.1 | 62.1 |
| 26.2 | 33.9 |
| 26.6 | 20.3 |
| 26.4 | 16.4 |
| 27.3 | 62.8 |
| 27.6 | 7.8 |

[1]The 2θ values were obtained using copper radiation (CuKα1 1.54060 Å)

Differential scanning calorimetry was carried out by means of a Mettler-Toledo DSC-822e calorimeter using aluminum crucibles, and a heating rate of 10° C./min, from 30° up to 300° C. The measurements were carried out in a dry nitrogen atmosphere using a 50 ml/min flow rate, The calorimeter was calibrated with indium of 99.99% purity.

The differential scanning calorimetry graph showed a weak exothermic peak with a maximum at 204-206° C., a sharp endothermic peak with an onset at 239° C. and a maximum at 240° C. (208 J/g).

Thermogravimetric analysis (TGA) was performed on a Mettler-Toledo SDTA851e thermobalance. Experimental conditions: alumina crucibles of 40 μl volume, atmosphere of dry nitrogen with 80 ml/min flow rate, heating rate of 10° C./min starting at 300 up to 300° C. In the thermogravimetric analysis no weight loss was observed before decomposition occurred. Weight loss due to decomposition was only observed at temperatures over 220° C., see FIG. 2.

FTIR spectrum was recorded on a Bruker Alpha spectrometer, equipped with a Bruker Diamond single reflection ATR system, a mid-infrared source as the excitation source and a DTGS detector. The spectrum were acquired in 32 scans with a resolution of 4 cm$^{-1}$ in the range of 4000-650 cm$^{-1}$. The IR spectrum obtained is characterised by the following bands: 3404, 3185, 3130, 1651, 1629, 1617, 1557, 1473, 1394, 1286, 1237, 1049, 1035, 796 and 640 (cm$^{-1}$).

Advantageously, the inventors have found that polymorphic form R-5 does not change by grinding, in the precedence of solvent or without solvent.

Grinding experiments were performed in a Retsch MM400 Ball Mill using the following methodology: samples of 30 mg of phase R-5 of Rufinamide were grinded at a frequency of 20 s$^{-1}$ for 15 min, with a drop of solvent and without solvent. The results obtained are shown in Table 2.

TABLE 2

| Initial solid | Solvent | Solids after grinding[1] |
|---|---|---|
| R-5 | — | R-5 |
| R-5 | Water | R-5 |
| R-5 | Ethanol | R-5 |
| R-5 | Isopropanol | R-5 |
| R-5 | 1-Propanol | R-5 |
| R-5 | 2-Butanol | R-5 |
| R-5 | Dichloromethane | R-5 |
| R-5 | 1,2-Dichloroethane | R-5 |
| R-5 | Tetrahydrofurane | R-5 |
| R-5 | Methyl ethyl ketone | R-5 |
| R-5 | Toluene | R-5 |

[1]The solid phase was determined by PXRD.

Further advantages of polymorphic form R-5 arose from the significant good thermal stability that has shown over time. No changes in polymorphic form was seen when form R-5 of rufinamide underwent accelerated degradation. Thermal stability experiments were performed in a Binder Vacuum oven VD53 using the following methodology. Samples of from R-5 of Rufinamide were kept under vacuum, at 40° C. for different periods of times (at 1 mbar), see table 3 below. There were no significant differences in the PXRD patterns of the solids obtained after the thermal treatment.

TABLE 3

| Entry | Initial solid | Temperature | Time | Solids after thermal treatment[1] |
|---|---|---|---|---|
| 1 | R-5 | 40° C. | 1 hour | R-5 |
| 3 | R-5 | | 24 hours | R-5 |
| 6 | R-5 | | 24 hours | R-5 |
| 9 | R-5 | | 24 hours | R-5 |
| 12 | R-5 | | 7 hours | R-5 |

[1]The solid phase was determined by PXRD.

Further experiments were carried out to study the effect of humidity on the stability of new form R-5. The relative humidity (RH) was set and controlled using a Projekt Messtechnik Modular Humidity Generator using the following methodology: samples of 10 mg of phase R-5 of Rufinamide were kept at 70% RH and at 50° C. for 24 hours and at 90% RH at 30° C. for 67 hours.

TABLE 4

| Entry | Initial solid | Relative humidity | Temperature | Time | Solids after humidity experiments[1] |
|---|---|---|---|---|---|
| 1 | R-5 | 70% | 50° C. | 24 hours | R-5 |
| 2 | R-5 | 90% | 30° C. | 67 hours | R-5 |

[1]The solid phase was determined by PXRD.

The polymorphic form R-5 of Rufinamide is also useful for obtaining other polymorphic forms of rufinamide. In particular, a new polymorphic form, referred as R-4, was also identified. Polymorphic form R-4 was characterised by means of PXRD, DSC and FTIR. The characteristic peaks of the PXRD of crystalline phase R-4 of Rufinamide are depicted in Table 5.

TABLE 5

| Angle 2θ[1] (°) | Relative Intensity % |
|---|---|
| 17.2 | 9.3 |
| 17.3 | 6.7 |
| 18.1 | 30.0 |
| 18.4 | 7.3 |
| 18.9 | 100.0 |
| 19.3 | 15.1 |
| 19.6 | 19.5 |
| 20.7 | 5.6 |
| 24.6 | 60.3 |
| 24.8 | 11.8 |
| 25.3 | 7.3 |
| 25.8 | 8.3 |
| 27.4 | 5.7 |
| 27.5 | 5.9 |
| 32.1 | 21.3 |
| 33.5 | 6.4 |
| 36.6 | 16.1 |

[1]The 2θ values were obtained using copper radiation ($Cu_{K\alpha 1}$ 1.54060 Å)

Characterisation by differential scanning calorimeter DSC (10° C./min) showed a sharp endothermic peak with an onset at 240° C. and a maximum at 240° C. (206 J/g). Measurements carried out by TGA (10° C./min) showed no weight loss before decomposition occurred. Weight loss due to decomposition occurred at temperatures over 220° C. The IR spectrum obtained for form R-4 is characterised by the following bands: 3408, 3179, 3086, 1627, 1595, 1560, 1472, 1397, 1282, 1234, 1037 and 797 $cm^{-1}$.

The new polymorphic form of Rufinamide, referred as form R-5, may be also prepared:

a) by bubbling with ammonia gas a solution of compound 1H-I activated as an acid chloride or, b) by adding a solution of compound 1H-I activated as an acid chloride over a mixture of ammonium chloride and concentrated aqueous ammonia solution The present invention is further illustrated by the following examples.

EXAMPLES

Comparative Example 1

Preparation of 1-(2,6-difluorobenzyl)-1H-1,2,3-triazole-4-carboxylic acid According to U.S. Pat. No. 4,789,680

Step 1. A solution of 0.200 g (1.23 mmol) of 2,6-difluorobenzyl chloride in 0.5 mL of DMSO was added dropwise to a mixture of 0.090 g (1.23 mmol) of $NaN_3$ in 2 mL of DMSO at 20-25° C. The reaction was left stirring at 20-25° C. during 4 h. until showing completion by TLC. The crude was treated with 1.6 mL of water and 1.6 mL of cyclohexane and the organic phase was vacuum distilled to obtain 0.210 g (97%) of 2,6-difluorobenzyl azide as yellowish oil Step 2. A mixture of 0.198 g (1.18 mmol) of 2,6-difluorobenzyl azide and 0.075 mL (1.20 mmol) of propiolic acid in 1.6 mL of toluene was heated at 70° C. over 24 h. After the reaction was cooled to 20-25° C. the brownish sticky solid was filtered, washed twice with 2 mL of $Et_2O$ and dried to obtain 0.226 g of a crude containing 1-(2,6-difluorobenzyl)-1H-1,2,3-triazole-4-carboxylic acid (purity by UPLC area: 87.57%, 3H-isomer: 2.85%).

Example 2

Preparation of 1-(2,6-difluorobenzyl)-1H-1,2,3-triazole-4-carboxylic acid

A suspension of 10.25 g (158 mmol) of NaN$_3$, 2.5 g (7.76 mmol) of tetrabutylammonium bromide and 25 g (154 mmol) of 2,6-difluorobenzyl chloride in 50 mL of isopropyl acetate was left stirring at 20-25° C. during 14 h until showing completion by TLC. The resultant mixture was washed with 10% NaCl aqueous solution at 0° C. to remove unreacted NaN$_3$ and the organic phase was stirred with a solution of 17.26 g (246 mmol) of propiolic acid in 50 mL of water at 50° C. during 8 h. After cooling to 20-25° C., the pH was adjusted to 3.2-3.4 by addition of 30% aqueous solution of NaOH and, after one hour at 20-25° C., the suspension was filtered. The solid was further washed with 25 mL of isopropyl acetate precooled at 0-5° C., washed with 40 mL of water dried at 200 mbar and 50° C. to obtain 21.52 g (57.4%) of 1-(2,6-difluorobenzyl)-1H-1,2,3-triazole-4-carboxylic acid (purity by UPLC area: 99.94%, 3H-isomer: 0.06%).

Example 3

Purification of 1-(2,6-difluorobenzyl)-1H-1,2,3-triazole-4-carboxylic acid

A stirred suspension of 8 g (33.5 mmol) of 1-(2,6-difluorobenzyl)-1H-1,2,3-triazole-4-carboxylic acid containing 6.7% of isomer 3H (UPLC area) was adjusted to pH 12.8 with 60 mL of 20% aqueous solution of NaOH. The clear solution so obtained was acidified to pH 3.3 with HCl 37% to precipitate a solid that once filtrated and dried at 50° C. under vacuum results 7.35 g (92%) of pure 1-(2,6-difluorobenzyl)-1H-1,2,3-triazole-4-carboxylic acid showing no detectable peak of isomer 3H in the UPLC chromatogram.

Example 4

Preparation of 1-(2,6-difluorobenzyl)-1H-1,2,3-triazole-4-carboxylamide Form R-5

To a suspension of 1 g (4.18 mmol) of 1-(2,6-difluorobenzyl)-1H-1,2,3-triazole-4-carboxylic acid in 2.5 mL of anhydrous THF at 0-5° C. under nitrogen atmosphere was added dropwise 0.36 mL (4.25 mmol) of oxalyl chloride. Afterwards, the mixture was left stirring at 20-25° C. during 2 h and then the obtained solution was added to a mixture of 0.95 mL (12.54 mmol) of 25% aqueous ammonia and 0.67 g (12.54 mmol) of ammonium chloride in 2.8 mL of water at 0-5° C. and few crystals of Form C. The precipitate formed was filtered and dried on a vacuum drier at 50° C. to obtain 0.68 g (68%) of 1-(2,6-difluorobenzyl)-1H-1,2,3-triazole-4-carboxylamide in a polymorphic Form C (checked by FTIR).

Example 5

Preparation of 1-(2,6-difluorobenzyl)-1H-1,2,3-triazole-4-carboxylamide Form R-5

To a suspension of 3 g (12.56 mmol) of 1-(2,6-difluorobenzyl)-1H-1,2,3-triazole-4-carboxylic acid in 15 mL of toluene was added 1.8 mL (24.73 mmol) of thionyl chloride and the mixture was left stirring at reflux during 4 h and a solution was obtained. The toluene and the excess of thionyl chloride was completely distilled off. 15 mL of fresh toluene was added to the residue and the mixture was cooled to 0-5° C. and ammonia gas was bubbled to obtain a suspension that was filtered and the solid was washed with water, isopropyl alcohol and again with more water. The solid was dried on a vacuum drier at 50° C. to obtain 1.67 g (55.9%) of 1-(2,6-difluorobenzyl)-1H-1,2,3-triazole-4-carboxylamide in a polymorphic Form C (checked by FTIR).

Example 6

Preparation of 1-(2,6-difluorobenzyl)-1H-1,2,3-triazole-4-carboxylamide Form R-5

To a suspension of 3 g (12.56 mmol) of 1-(2,6-difluorobenzyl)-1H-1,2,3-triazole-4-carboxylic acid in 15 mL of anhydrous THF at 0-5° C. was added 1.1 mL (12.72 mmol) of oxalyl chloride and the mixture was left stirring at 20-25° C. during 4 h and a solution was obtained. The mixture was bubbled with ammonia gas to obtain a suspension that was cooled at 0-5° C. during 1 h, filtered and the solid was washed with water. The solid was dried on a vacuum drier at 50° C. to obtain 0.694 g (23.2%) of 1-(2,6-difluorobenzyl)-1H-1,2,3-triazole-4-carboxylamide in a polymorphic Form C (checked by FTIR).

Example 7

Preparation of 1-(2,6-difluorobenzyl)-1H-1,2,3-triazole-4-carboxamide (Rufinamide polymorphic form R-5)

1.9 ml (22.4 mmol) of oxalyl chloride were added drop wise, to a suspension of 5 g (20.9 mmol) of 1-(2,6-difluorobenzyl)-1H-1,2,3-triazole-4-carboxylic acid in 12.5 ml of anhydrous THF, at 20-25° C. and under nitrogen atmosphere. Once the addition of oxalyl chloride was completed, the mixture was stirred at 20-25° C. for 4 h. Afterwards, the resulting mixture was concentrated under vacuum to dryness, in order to eliminate HCl and unreacted oxalyl chloride. The obtained residue was dissolved in ml of fresh anhydrous THF and treated with 4.0 g (75.2 mmol) of ammonium chloride and 5.26 g (62.7 mmol) of sodium bicarbonate over 16 h at 20-25° C. The resultant suspension was treated with 30 ml of water. The solid was filtrated and washed with 30 ml of a saturated aqueous sodium bicarbonate solution and twice with 30 ml of water. The solid was dried in a vacuum drier at 50° C. to yield 2.78 g (55.8%) of 1-(2,6-difluorobenzyl)-1H-1,2,3-triazole-4-carboxamide as Form R-5.

Example 8

Preparation of 1-(2,6-difluorobenzyl)-1H-1,2,3-triazole-4-carboxamide (Rufinamide polymorphic form R-5)

3.74 ml (45.65 mmol) of oxalyl chloride were added drop wise to a suspension of 10 g (41.8 mmol) of 1-(2,6-difluorobenzyl)-1H-1,2,3-triazole-4-carboxylic acid in ml of anhydrous THF, at 20-25° C. and under nitrogen atmosphere. When the addition of oxalyl chloride was concluded, the mixture was stirred at 20-25° C. for 4 h. Afterwards, the resulting mixture was diluted with 50 ml of anhydrous THF, followed by the distillation of 15 ml at 35-40° C. under vacuum, in order to remove the remaining HCl. The reaction was cooled to 20-25° C. and 8 g (149.57 mmol) of ammonium chloride were added followed by addition of 20 ml of 8% aqueous solution of sodium bicarbonate. After further addition of 8.8 g (104.97 mmol) of sodium bicarbonate, the mixture was left under powerful stirring over 4 h at 20-25° C. To conclude with, the suspension was filtered and washed twice with 50 ml of a saturated aqueous sodium bicarbonate solution and twice with 50 ml of water The solid was dried on a vacuum drier at 50° C. to yield 5.6 g (56.2%) of 1-(2,6-difluorobenzyl)-1H-1,2,3-triazole-4-carboxamide as Form R-5.

Example 9

Preparation of 1-(2,6-difluorobenzyl)-1H-1,2,3-triazole-4-carboxamide (Rufinamide polymorphic form R-5)

75.4 ml of Oxalyl chloride (919.8 mmol) were added at 25° C. to a stirred suspension of (2,6-difluorobenzyl)-1H-1,2,3-triazole-4-carboxylic acid (200.0 g, 836.2 mmol) in THF (500 ml) and DMF (0.5 ml). The stirring was maintained for 4 hr at 25° C. until the solid dissolved. Afterwards, 1000 ml of THF were added and reduced pressure (200-250 mbar) was applied leading to the distillation of 300 ml of THF and to the maintenance of the internal temperature at about 25-35° C. After that, the mixture was slightly cool to 25° C. and 160 g of ammonium chloride were added in portions followed by slow addition of 400 ml of an 8% NaHCO3 solution and 176 g of solid NaHCO3 (vigorous stirring was also needed to prevent frothing). The heterogeneous mixture was stirred for 2 hr, filtered and the solid re-suspended in 1 L water. The solid was filtered and dried (at 200 mbar/50° C.) yielding 130 g (65.3%) of 1-(2,6-difluorobenzyl)-1H-1,2,3-triazole-4-carboxamide, as a white solid in form R5.

Example 10

Preparation of 1-(2,6-difluorobenzyl)-1H-1,2,3-triazole-4-carboxamide (Rufinamide polymorphic form R-4)

A suspension of Rufinamide form R-5 (110 mg, 0.46 mmol) in a 1:1 mixture of methanol and water (35 mL) was heated at reflux for one hour. The solution obtained was cooled down to 20° C. in four hours without stirring. The resulting suspension was filtered off and the white solid obtained was dried under vacuum (1 mbar) at 40° C. for 4 hours (80 mg, 73% yield). The solid was analyzed by PXRD and corresponded to phase R-4.

Example 11

Preparation of 1-(2,6-difluorobenzyl)-1H-1,2,3-triazole-4-carboxamide (Rufinamide polymorphic form R-4)

A suspension of Rufinamide, polymorphic form A, (100 mg, 0.42 mmol) in a 1:1 mixture of methanol and water (37 mL) was heated at reflux for one hour. The solution obtained was cooled down to room temperature in ten hours without stirring. The resulting suspension was filtered off and the white solid obtained was dried under vacuum (1 mbar) at 40° C. for 1 hour (75 mg, 75% yield). The solid was analyzed by PXRD and corresponded to phase R-4.

What is claimed is:
1. A process for preparing rufinamide

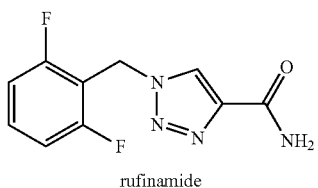 [SMILES: NC(=O)c1cn(Cc2c(F)cccc2F)nn1]

rufinamide which comprises the one-pot process for the preparation of a compound of formula 1H-I

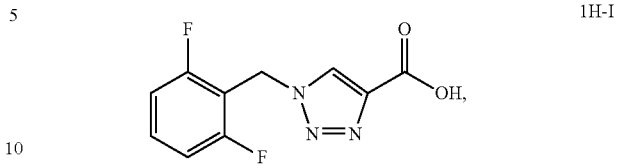

said process comprising the steps of:
a) reacting a compound of formula IX

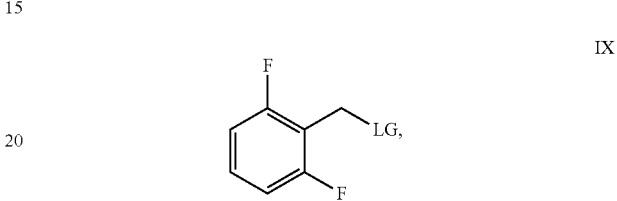

with sodium azide in the presence of a phase transfer catalyst and a non polar solvent or a dipolar aprotic solvent having a boiling point below about 100° C., wherein LG is a leaving group;
b) reacting the resulting mixture with propiolic acid;
c) isolating the compound of formula 1H-I, wherein the compound of formula 1H-I comprises an 3H-I isomer of the formula

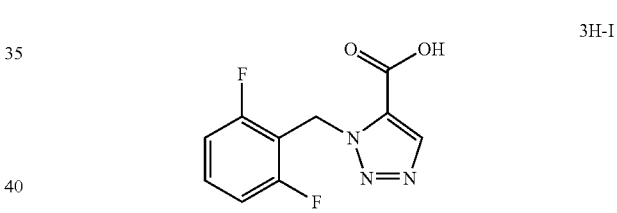

in an amount less than about 0.2 area-% as measured by a chromatographic method, and
d) activating the compound of formula 1H-I in the form of an acid halide;
e) reacting the produce of step d) with ammonia ore a solution comprising ammonia; and
f) isolating the rufinamide.
2. The process of claim 1, wherein the non polar solvent in step a) is selected from heptane, methyl cyclohexane, hexane, pentane, toluene, and mixtures thereof.
3. The process of claim 1, wherein the dipolar solvent in step a) is selected from ethyl acetate, isopropyl acetate, acetone, tetrahydrofuran, and mixtures thereof.
4. The process of claim 1, wherein step a) is performed at a temperature between about 0° C. and about 100° C.
5. The process of claim 1, wherein the phase transfer catalyst in step a) is selected from tetralkylammonium salts, 18-crown-6, phosphonium salts, cryptands, and doped clays.
6. The process of claim 5, wherein the phase transfer catalyst is tetra-n-butylammonium bromide.
7. The process of claim 1, wherein the leaving group is selected from halogens and activated alcohols.
8. The process of claim 1, wherein the propiolic acid of step b) is added to the mixture directly, with water in the form of a solution, with an organic solvent, or with mixtures thereof.

9. The process of claim 8, wherein the organic solvent is a polar solvent selected from methanol, ethanol, isopropanol, butanol, and mixtures thereof.

10. The process of claim 1, wherein step b) is performed at a temperature between about 20° C. and about 65° C.

11. The process of claim 1, wherein step b) is performed at a temperature between about 50° C. and about 55° C.

12. The process of claim 1, wherein step c) comprises the precipitation of the compound of formula 1H-I at a pH value between about 3.0 and about 4.5.

13. The process of claim 1, wherein step c) comprises the precipitation of the compound of formula 1H-I at a pH value between about 3.2 and about 4.2.

14. The process of claim 1, further comprising step d) purifying the isolated compound of formula 1H-I from step c) by dissolving said isolated compound 1H-I at a pH greater than about 12 and precipitating said isolated compound at a pH value between about 3.2 to about 4.0.

* * * * *